(12) United States Patent
Montagnier

(10) Patent No.: US 9,133,525 B2
(45) Date of Patent: Sep. 15, 2015

(54) DETECTION OF DNA SEQUENCES AS RISK FACTORS FOR HIV INFECTION

(71) Applicant: Luc Montagnier, Le Plessis (FR)

(72) Inventor: Luc Montagnier, Le Plessis (FR)

( * ) Notice: Subject to any disclaimer, the term of this patent is extended or adjusted under 35 U.S.C. 154(b) by 12 days.

(21) Appl. No.: 13/752,003

(22) Filed: Jan. 28, 2013

(65) Prior Publication Data

US 2013/0196939 A1    Aug. 1, 2013

Related U.S. Application Data

(60) Provisional application No. 61/716,123, filed on Oct. 19, 2012, provisional application No. 61/591,111, filed on Jan. 26, 2012.

(51) Int. Cl.

| | |
|---|---|
| *C12P 19/34* | (2006.01) |
| *C12Q 1/68* | (2006.01) |
| *C12N 1/20* | (2006.01) |
| *A61K 31/7052* | (2006.01) |
| *A61K 31/65* | (2006.01) |
| *C12Q 1/70* | (2006.01) |
| *C12N 15/11* | (2006.01) |

(52) U.S. Cl.
CPC ............... *C12Q 1/689* (2013.01); *A61K 31/65* (2013.01); *A61K 31/7052* (2013.01); *C12N 1/20* (2013.01); *C12Q 1/703* (2013.01); *C12N 15/11* (2013.01)

(58) Field of Classification Search
CPC ... A61K 31/65; A61K 31/7052; C12N 15/11; C12N 1/20; C12Q 1/689; C12Q 1/703
USPC ....................................................... 435/91.2
See application file for complete search history.

(56) References Cited

U.S. PATENT DOCUMENTS

| | | | | |
|---|---|---|---|---|
| 2004/0111221 | A1* | 6/2004 | Beattie et al. ................ | 702/20 |
| 2006/0057699 | A1 | 3/2006 | Munderloh | |
| 2007/0218489 | A1* | 9/2007 | Sampath et al. .............. | 435/6 |
| 2010/0041011 | A1 | 2/2010 | Van Agthoven et al. | |
| 2011/0027774 | A1 | 2/2011 | Montagnier | |
| 2011/0184025 | A1 | 7/2011 | Hensel | |

FOREIGN PATENT DOCUMENTS

WO    WO 2010144695    * 12/2010

OTHER PUBLICATIONS

International Search Report and Written Opinion of the International Searching Authority with Search History Issued Jul. 9, 2013 in PCT/US2013/023451.
Guy H. Palmer et al., "Detection of an *Anaplasma marginale* Common Surface Protein Present in All Stages of Infection", Journal of Clinical Microbiology, vol. 23, No. 6, Jun. 1986, pp. 1078-1083 with cover page.
Varda Shkap et al., "Expression of Major Surface Protein 2 Variants with Conserved T-Cell Epitopes in *Anaplasma centrale* Vaccinates", Infection and Immunity, vol. 70, No. 2, Feb. 2002, pp. 642-648.
Kelly A. Brayton et al., "Complete genome sequencing of *Anaplasma marginate* reveals that the surface is skewed to two superfamilies of outer membrane proteins", PNAS, vol. 102, No. 3, Jan. 18, 2005, pp. 844-849.

* cited by examiner

*Primary Examiner* — Cynthia B Wilder
(74) *Attorney, Agent, or Firm* — Steven M. Hoffberg, Esq.; Ostrolenk Faber LLP

(57) ABSTRACT

A method for identifying a risk factor for diseases, disorders or conditions, such as those caused by human immunodeficiency virus, using the polymerase chain reaction and specific primers. Methods for treating patients having these diseases, disorders or conditions by antimicrobial treatment of the risk factor by combined antiviral and antibacterial treatment or by sustaining or stimulating the subject's immune system. Methods for screening biological products including red blood cell preparations. Primers and methods for detecting nucleic acids or microbial agents associated with red blood cells, such as those associated with red blood cells in subjects infected with HIV and undergoing antiretroviral therapy.

20 Claims, 2 Drawing Sheets

```
                           SEQUENCE LISTING

<160> NUMBER OF SEQ IDS NOS: 33

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gcaacgcgaa aaaccttacc                                                  20

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
gacgggcagt gtgtacaa                                                    18

<210> SEQ ID NO 3
<211> LENGTH: 18
<212> TYPE: DNA
<213> ORGANISM: Artificial Sequence
<220> FEATURE:
<223> OTHER INFORMATION: Primer

<400> SEQUENCE: 3
gcctacagat taaaggct                                                    18

<210> SEQ ID NO 4
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 4
atcatartca ccatcaccta                                              20

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
cytacagagt gaaggct                                                 17

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
atcatartca ccatcaccta                                              20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
ccttacactc agccagacat                                              20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ccaggtgtgt ggcttataca                                              20

<210> SEQ ID NO 9
<211> LENGTH: 25
<212> TYPE: DNA
<213> ORGANISM: Artificial Sequence
<220> FEATURE:
<223> OTHER INFORMATION: Primer

<400> SEQUENCE: 9
catagcttcc tagtaagtag accag                                        25

<210> SEQ ID NO 10
<211> LENGTH: 18
<212> TYPE: DNA
<213> ORGANISM: Artificial Sequence
<220> FEATURE:
<223> OTHER INFORMATION: Primer

<400> SEQUENCE: 10
aggggagtct gagatggt                                                18

<210> SEQ ID NO 11
<211> LENGTH: 18
```

```
<212> TYPE: DNA
<213> ORGANISM: Artificial Sequence
<220> FEATURE:
<223> OTHER INFORMATION: Primer

<400> SEQUENCE: 11
actggagagg tggaggtt                                                    18

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ggtaattcct atgtgcgagg t                                                21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
tcaaaagaca gtggtgactc t                                                21

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
atgtctggct gagtgtaagg                                                  20

<210> SEQ ID NO 15
<211> LENGTH: 24
<212> TYPE: DNA
<213> ORGANISM: Artificial Sequence
<220> FEATURE:
<223> OTHER INFORMATION: Primer

<400> SEQUENCE: 15
atgtagttga gcagttttga atga                                             24

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
tcctgcctta gtgaggatct                                                  20

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
```

```
atgaataggt gatggtgatg act                                            23
```

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18

```
ccgtcattta agcctttaat ctca                                           24
```

<210> SEQ ID NO 19
<211> LENGTH: 24
<212> TYPE: DNA
<213> ORGANISM: Artificial Sequence
<220> FEATURE:
<223> OTHER INFORMATION: Primer

<400> SEQUENCE: 19

```
gtagtctttt ggcatctctt tgta                                           24
```

<210> SEQ ID NO 20
<211> LENGTH: 19
<212> TYPE: DNA
<213> ORGANISM: Artificial Sequence
<220> FEATURE:
<223> OTHER INFORMATION: Primer

<400> SEQUENCE: 20

```
cagcctggag aacagagtg                                                 19
```

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21

```
gatctagcag ttcataggaa ggaa                                           24
```

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22

```
ggctgaaaca atggggtttt                                                20
```

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23

```
tttagtagac ccctcgacca                                                20
```

<210> SEQ ID NO 24
<211> LENGTH: 17
<212> TYPE: DNA
<213> ORGANISM: Artificial Sequence

```
<220> FEATURE:
<223> OTHER INFORMATION: Primer

<400> SEQUENCE: 24
ctgacgacag ccatgca                                                   17

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gcagtgggga atattggaca                                                20

<210> SEQ ID NO 26
<211> LENGTH: 237
<212> TYPE: DNA
<213> ORGANISM: Artificial Sequence
<220> FEATURE:
<223> OTHER INFORMATION: 237 bp amplicon generated with MSP2 primer #3
      and MSP2 primer #5 by PCR

<400> SEQUENCE: 26
atcatagtca ccatcaccta ccagctgtat aagccacaca cctgggagtc ctcctagcct     60 tttcctcct cctctcatcc tccatatccc attgaccgtc agggcctact gagtctacac    120
tccaattttc ttttaaatct atccccactg ccactgtcct agtctaaggc aataccatct   180
ggtcacccag atcattccat agcttcctag taagtagacc agccttcact ctgtaag      237

<210> SEQ ID NO 27
<211> LENGTH: 213
<212> TYPE: DNA
<213> ORGANISM: Artificial Sequence
<220> FEATURE:
<223> OTHER INFORMATION: 213 bp amplicon generated with MSP2 primer #2
      and MSP2 primer #5 by PCR

<400> SEQUENCE: 27
gcctacagat taaaggctta aatgacggtg aaaacttagt attctttggg tggacaatag     60
tgaaatttgc actttggaca gaatgacatg tacaaaaaga gtcaagaaac ttttaatct    120 atttaaagga ctcaaagtaa tttgtgaagg ccatagcgta aaataacttc agtggatgga   180
atgggatgat gaataggtga tggtgactat gat                                213

<210> SEQ ID NO 28
<211> LENGTH: 546
<212> TYPE: DNA
<213> ORGANISM: Artificial Sequence
<220> FEATURE:
<223> OTHER INFORMATION: 546 bp amplicon of genomic human chromosome 1
      amplified by primers hChr1/14179308 S and hChr1/14179853 AS

<400> SEQUENCE: 28
ccttacactc agccagacat atatttgtgt tttgttatcc atgtgcacag agactttggc     60
attctgggtg aaggaagaaa gaagagaata tacatggaaa cccagggta agagaaaagg    120 acaacagaga atgtggcatg gggaatgctc tgctgggtca cattgaatgg ttctgaacca   180
ctgtggaaaa aaaggagtta gaaagaatca gatgccgaag gagccaattt tcacaatact   240
ccgagactca gggcaaaagc agccttgttc tagtagccta tgggtaaaag aagacacaga   300
actgagggga ggactttcc cctgagtcca ccacaaaccg ccatggagct gaggcagcct    360
```

```
gaagtctcag gggcatggga gggatttgcc ttttggattt ctccaatggg atgtcttaca    420
ggcacttcat atttagcaga tccaaaactt aactcagata ctcctcttgc catatctgtt    480
cctcttgctg tgttcctgac catgattatc accatcacct accagctgta taagccacac    540
acctgg                                                               546
```

<210> SEQ ID NO 29
<211> LENGTH: 1644
<212> TYPE: DNA
<213> ORGANISM: Artificial Sequence
<220> FEATURE:
<223> OTHER INFORMATION: 1644 bp amplicon of genomic human chromosome 7
      amplified by primers hChr7/4292976 S and hChr7/4294619 AS

<400> SEQUENCE: 29

```
atgtagttga gcagttttga atgagtttct taatcctgag ttctagttta agaaaatatt     60
aaaaataaaa aattatgtca ccaactaaat ttttactgca gataatcata agttggttag    120
attggacctt cattgtgaaa tgcagtaact ttggtttaag caatatccaa aaccagaaat    180
tggtcgaggg gtctactaaa ttccgttttc ttttgttcta aacaattaaa cattctaaaa    240
tttagggaaa aggaccaatg gtgcaaacat tttagagctg acagttgtgt gccatatgcc    300
atgattctgt tacaaatgaa cagtattcag attcaaaatc agtgtaaaca ctgtgtgtgt    360
gtgtgtgtgt gtgtgtgtgt gtgtgtgtgt gtattttaca cagccattta aatattaacc    420
gcctttgagt attaggggaa aaaacagaaa ctaaaagcga atatatttgt tcctgaatcc    480
tcccaccaaa ccactttta aattaattat atttcctgcc ttagtgagga tcttcctatt    540
catcaaagat aaaataccaa atataattta ctctccttct ctacctcacc cccaatattc    600
aacaattccc tattttattt tgattttact tcctattgtc tctcagtgca tccttactac    660
tggtttctgg cctcaatgtc tctttccata atacttcct ccagggcttc agcagtgtat    720
attgcaatcc atgagtgtga tgcccttata agctgtacag gcacaaccca ggcaaacata    780
cacaatgacc ataatcataa cagtcattac tggtgccttt actctggttt tatccatccc    840
ccaacaatcc tttaatcctc cactagagtt tattctttta agtgaaaatc tggattctta    900 tctccctag tatgtatctc ttagtgaatt tttatatgag atagtcatca ccatcaccta    960
ttcatcatcc cattccatcc actgaagtta ttttacgcta tggccttcac aaatttactt   1020
tgagtccttt aaatagatta aaaagtttct tgactctttt tgtacatgtc attctgtcca   1080
aagtgcaaat ttcactattg tccacccaaa gaatactaag ttttcaccgt catttaagcc   1140
tttaatctca ggatctcaca ataaatacaa tcactctttc ctatatgcct aatcttctgc   1200
ttgagcataa ttttaatgtg ctaactattc tgtaattata tatatatttt taattcagcc   1260
acttctctca ctagaaagtg agtttgttga aatcagggta agtatatttt atgtttggat   1320
gaattcccca tcacaatact tcacatgtag ttatctagtc accaattttt attgaaatta   1380
attgtacata taataaaact ttaatataaa atgtttctct tgaggggaga ttttctttgt   1440
aaaactatcc ttctgagctt tgtgatgtga tgattgtcta atgtctgttg caagattaag   1500
gaaaatgtat ttgaatgcaa atgaacttac actgtcatac caaagtgtg ataatttctt   1560 gctcctgaac tcactctccc tacctgccta ttaaaatcag aatacacaga tctgtatctg   1620
tacaaagaga tgccaaaaga ctac                                          1644
```

<210> SEQ ID NO 30
<211> LENGTH: 396

<212> TYPE: DNA
<213> ORGANISM: Artificial Sequence
<220> FEATURE:
<223> OTHER INFORMATION: 396 bp amplicon of genomic human chromosome 1
      amplified by primers hChr1/14180006 S and hChr1/14180401 AS

<400> SEQUENCE: 30

```
catagcttcc tagtaagtag accagccttc agtctgagcc ctcctcggtc cttcctcccc      60
agtgctgctg gagtaatcct tctaacacaa caatgaaagc aggtcactgc ggctcaaatg     120
atgtcagcgg ctttatcatc catgttgcct ggcttttcac aggcatgtct tgcagtgcag     180
ccttataact ctctcaacac aactctgtat cctcctcatt cttcatgctt ttataatgtc     240
aagccatgtg acactcccta aatataccat gttttctctt tttcctcctc ccctctctc     300
atttgcagct tcccatactt atcttcctaa acactactct ttttgaaatg tttatttcaa     360
gggtttctta tcttttaaac catctcagac tcccct                              396
```

<210> SEQ ID NO 31
<211> LENGTH: 1088
<212> TYPE: DNA
<213> ORGANISM: Artificial Sequence
<220> FEATURE:
<223> OTHER INFORMATION: 1088 bp amplicon of genomic human chromosome 1
      amplified by primers hChr1/14180006 S and hChr1/14181093 AS

<400> SEQUENCE: 31

```
catagcttcc tagtaagtag accagccttc agtctgagcc ctcctcggtc cttcctcccc      60
agtgctgctg gagtaatcct tctaacacaa caatgaaagc aggtcactgc ggctcaaatg     120
atgtcagcgg ctttatcatc catgttgcct ggcttttcac aggcatgtct tgcagtgcag     180
ccttataact ctctcaacac aactctgtat cctcctcatt cttcatgctt ttataatgtc     240
aagccatgtg acactcccta aatataccat gttttctctt tttcctcctc ccctctctc     300
atttgcagct tcccatactt atcttcctaa acactactct ttttgaaatg tttatttcaa     360
gggtttctta tcttttaaac catctcagac tcccctgggg attacccctt ttcctatgtt     420
tttattgtag catcctcaca aattcacttt agttccttcg cattctggtg tcgctatata     480
ttagtgggac tatgtcccca ttaacctgtt agatctcttg agaaaaggga catgtctttt     540
catcttgagt tccccaatac ttagtattgt gcttagcata tgctaggtgc tcagtaaata     600
tttgatatgt gtgtgaacga atgaatcaat caatcaataa caaatgacag acaaactcca     660
accccaaac ctaaaaaaaa aaaatccaaa ctttccccctt gctcttagtg tagatactgc     720
tcatcaacat aaggcaaatt cttcctgcgc gtctcaatac agaggaggcg agaactcaca     780
gaatcacaga attagagcac tggctttggc atgagaacac cctgagttaa aatctggctt     840
ctgctattta ttagccacat gacagtgaat ctccttgagc ttctgttttg tacaaactta     900
agtttggctt tgtgatctta ttcctctttg gtgcatctgt acacccaac tgcttattca      960
tatgacactg ctaaaacatg ccttgccttc tcccccactt ttttttttgg agacagaatc    1020
tcccttttgtc acccaggctg gaattcagtg gcgtgatctc ggctcactgc aacctccacc    1080
tctccagt                                                            1088
```

<210> SEQ ID NO 32
<211> LENGTH: 1494
<212> TYPE: DNA
<213> ORGANISM: Artificial Sequence
<220> FEATURE:
<223> OTHER INFORMATION: 1494 bp amplicon of genomic human chromosome 7
      amplified by primers hChr7/4293490 S and hChr7/4294983 AS

<400> SEQUENCE: 32

```
tcctgcctta gtgaggatct tcctattcat caaagataaa ataccaaata taatttactc    60
tccttctcta cctcacccc aatattcaac aattccctat tttattttga ttttacttcc    120
tattgtctct cagtgcatcc ttactactgg tttctggcct caatgtctct ttccataaat    180
acttcctcca gggcttcagc agtgtatatt gcaatccatg agtgtgatgc ccttataagc    240
tgtacaggca aacccaggc aaacatacac aatgaccata atcataacag tcattactgg    300
tgcctttact ctggttttat ccatccccca acaatccttt aatcctccac tagagtttat    360
tcttttaagt gaaaatctgg attcttatct cccctagtat gtatctctta gtgaattttt    420
atatgagata gtcatcacca tcacctattc atcatcccat tcatccact gaagttattt    480
tacgctatgg ccttcacaaa ttactttgag tcctttaaat agattaaaaa gtttcttgac    540
tcttttgta catgtcattc tgtccaaagt gcaaatttca ctattgtcca cccaaagaat    600
actaagttt caccgtcatt taagccttta atctcaggat ctcacaataa atacaatcac    660
tctttcctat atgcctaatc ttctgcttga gcataatttt aatgtgctaa ctattctgta    720
attatatata tatttttaat tcagccactt ctctcactag aaagtgagtt tgttgaaatc    780
agggtaagta tattttatgt ttggatgaat tccccatcac aatacttcac atgtagttat    840
ctagtcacca attttattg aaattaattg tacatataat aaaactttaa tataaaatgt    900
ttctcttgag gggagatttt ctttgtaaaa ctatccttct gagctttgtg atgtgatgat    960
tgtctaatgt ctgttgcaag attaaggaaa atgtatttga atgcaaatga acttacactg    1020
tcataccaaa agtgtgataa tttcttgctc ctgaactcac tctccctacc tgcctattaa    1080
aatcagaata cacagatctg tatctgtaca aagagatgcc aaaagactac tttcatgctg    1140
caacatgatt atgtgccccc aaaacctgga tatttatagt atagtatcca gtattttcaa    1200
tctaagctgt actggagccc gaagctaaag gaaaattagt aatactgatg ctccctttat    1260
ttaaacttt aagactttat catggcatta attttgactt taaaaatat tatcattttt    1320
tttggaccc cttaaatttt gttcccgagt tgaatgcctc actgggactt gggtgaatga    1380
atgctcaccc tagtcctaga ttaggtactc atcttaaata ctgttagttt ggggtggttt    1440
tttttttttt ttttttttt tttttgacag agcctcactc tgttctccag gctg           1494
```

<210> SEQ ID NO 33  
<211> LENGTH: 681  
<212> TYPE: DNA  
<213> ORGANISM: Artificial Sequence  
<220> FEATURE:  
<223> OTHER INFORMATION: 681 bp amplicon of HIV-negative subject amplified by primers of SEQ ID NOs: 24 and 25

<400> SEQUENCE: 33

```
gcacctgtat gtgaattccc gaaggcactc ccgcatctct gcaggattct cactatgtca    60
agaccaggta aggttcttcg cgttgcatcg aattaaacca catgctccac cgcttgtgcg    120
ggcccccgtc aattcatttg agttttaacc ttgcggccgt actccccagg cggtctactt    180
atcgcgttaa ctgcgccact aaagtctcaa ggacccaac ggctagtaga catcgtttac    240
ggcgtggact accagggtat ctaatcctgt ttgctaccca cgctttcgaa tctcagtgtc    300
aatattatgc caggaagctg ccttcgccat cggcattcct ccagatctct acgcatttca    360
ccgctacacc tggaattcta cttccctctc acatattcta gcaccaccag tatcacatgc    420
agttcccagg ttaagcccgg ggatttcaca tgtgacttaa tgagccacct acactcgctt    480
```

```
tacgcccagt aattccgatt aacgctcgca ccctctgtat taccgcggct gctggcacag     540
agttagccgg tgcttattct gcaggtaacg tctaatctaa tgggtattaa ccattagcct     600
ctcctccctg cttaaagtgc tttacaacca aaaggccttc ttcacacacg cggcatggct     660
ggatcagggt tgcccccccat t                                              681
```

DETECTION OF DNA SEQUENCES AS RISK FACTORS FOR HIV INFECTION

CROSS-REFERENCE TO RELATED APPLICATIONS

This application claims priority under 35 U.S.C. §119(e) to U.S. Provisional Application 61/716,123, filed Oct. 19, 2012 and to U.S. Provisional Application 61/591,111, filed Jan. 26, 2012, which are hereby incorporated by reference. The subject matter disclosed in U.S. Application Nos. 61/186,610; 61/358,282; 61/476,110; 61/476,545; 12/797,286; 13/168,367; 61/591,111; and PCT/US2010/038160 is hereby incorporated by reference.

STATEMENT REGARDING FEDERALLY SPONSORED RESEARCH OR DEVELOPMENT (None)

REFERENCE TO MATERIAL ON COMPACT DISK (None)

BACKGROUND OF THE INVENTION

1. Field of the Invention

DNA can be amplified from human red blood cell samples by primers designed from DNA sequences encoding a bacterial major surface protein and 16 s ribosomal RNA (16s rRNA). Primer pairs based on DNA sequences for the major surface protein 2 (MSP2) of Ehrlichia/Anaplasma can amplify DNA homologous to DNA from human chromosomes 1 and 7 from red blood cell samples. Primers based on DNA sequences encoding 16s rRNA from Anaplasma species can amplify DNA from human red blood cells, but not from nucleated white blood cells. The amplified DNA is contained in samples of red blood cells from HIV infected individuals as well as from some healthy individuals of Caucasian or African origin and represents a risk factor for HIV infection. These primers can be employed in methods for assessing risk of HIV infection by amplifying DNA from red blood cell samples.

2. Description of the Related Art

Chronic HIV infection causes strong immune depression (AIDS) in most patients leading to lethal opportunistic infections or cancers. Specific inhibitors of HIV multiplication are currently used for treating HIV infected patients before they reach the full-blown stage of AIDS. Such inhibitors act mostly on the reverse transcriptase and protease of HIV to efficiently suppress virus multiplication and reduce virus load to a low level of less than 40 viral RNA copies per ml of blood. Treatment results in a partial recovery of the patient's immune system as evidenced by an increase of CD4 lymphocytes and reduction of or lessened severity of opportunistic infections. However, this treatment has to be given without interruption in order to prevent rebound of virus multiplication and a subsequent reduction in the numbers of CD4 lymphocytes. Rebound of viral infection is evidence of a reservoir of HIV in infected patients that is not accessible to antiviral treatment and the existence of this reservoir is generally acknowledged. In addition to a reservoir of HIV in infected patients, such patients often carry other microorganisms that are associated with HIV infection or that cause opportunistic infections.

Microorganisms associated with HIV infection that are detectable in human red blood cells, but not in human leukocytes or other kinds of nucleated human cells have not been previously characterized. The identification and characterization of microorganisms associated with HIV infection is of interest for purposes of assessing risk of HIV infection or determining the status of an HIV infected patient, for assessing risk or status of opportunistic infections, and to evaluate modes of treatment for HIV infected subjects.

BRIEF SUMMARY OF THE INVENTION

The primers designed and discovered by the inventor provide ways to pursue these objectives. Three kinds of primers have been developed and studied by the inventor.

The first kind of primer was designed based on the gene encoding the outer surface protein 2 of Ehrlichia/Anaplasma a genus of rickettsiales, which are known endosymbionts of other cells. These primers amplified DNA homologous to segments of DNA from human chromosomes 1 and 7. These primers are described in Appendix 2.

This first kind of primers were initially designed to detect DNA encoding the major surface protein 2 (MSP2) of Ehrlichia/Anaplasma species. However, neither of the two pairs of primers described by Appendix 2 (Primer Pairs 1 and 2) detected at various annealing temperatures any related microorganism in the biological samples investigated.

Surprisingly, it was discovered that this first kind of primer amplified DNA from human red blood cell samples that was highly homologous to DNA sequences on segments of human chromosomes 1 and 7. Primer Pairs 1 and 2 amplified DNA by the polymerase chain reaction ("PCR") that was 100% homologous with human sequences when the primer sequences themselves were excluded. The amplified DNA was sequenced and the sequences aligned to sequences described for human chromosome 1 (clone RP11-332J14 GI:22024579, clone RP11-410C4 GI:17985906, and Build GRCh37.p5 Primary Assembly —) and in human chromosome 7 (PAC clone RP4-728H9 GI:3980548; human Build GRCh37.p5, and alternate assembly HuRef SCAF_1103279188381:28934993-35424761). This was not expected since the primer pairs had been designed to detect genes encoding a bacterial MSP2 gene, not human chromosomal sequences. Furthermore, the amplification of such sequences from samples of red blood cells was in itself surprising since red blood cells lack a nucleus containing chromosomes. The ability to amplify DNA homologous to human DNA from red blood cells is evidence that the target DNA amplified by these primers is present as an extranuclear or cytoplasmic element, such as a plasmid, or is contained in or bound by a microorganism that invades or is otherwise associated with red blood cells. This DNA component may be present on a plasmid or otherwise contained in or bound to a microbe associated with red blood cells. Its presence represents a risk factor for HIV infection or progression and/or opportunistic infections.

A second kind of primer was designed based on the sequences homologous to human chromosomes 1 and 7 that were amplified by the first kind of primers (MSP2 primers). This kind of primer is useful for identifying the target DNA homologous to human chromosomes 1 and 7 in a sample, such as a red blood cell sample. Such primers, including the first type of MSP2 primers, are used to detect risks of HIV infection, HIV progression, risks of opportunistic infections, disease prognosis and response to drug treatment in subjects where the presence of DNA homologous to segments human chromosomes 1 and 7 is a risk factor. This kind of primer is exemplified in Appendix 3.

A third type of primer was developed based on the genes from *Anaplasma* species encoding 16s rRNA. *Anaplasma* is a genus of rickettsiales. This type of primer was found to amplify a sequence of 700 bp of ribosomal DNA that was about 85% identical to the corresponding genetic regions of *Rickettsia* and about 99% identical to the corresponding genetic regions of *Acinetobacter* genus. *Acinetobacter* is a genus of gram negative bacteria within the class of gammaproteobacteria. The homology of amplified 16s rDNA with *Acinetobacter* DNA may be coincidental because DNA can be amplified from biological samples that pass through a 450 nM filter unlike classical Acinetobacteria.

These primers identify a bacterial agent associated with red blood cells that is related to but not identical to known *Rickettsia* species. This bacterial agent has been identified in red blood cells of not only HIV infected patients but also in some healthy individuals of Caucasian or African origin. This third type of primer is used to detect risks of HIV infection, HIV progression, risks of opportunistic infections, disease prognosis and response to drug treatment in subjects where the presence of a target containing the amplifiable 16s rRNA or 16s rDNA is a risk factor. These primers are described in Appendix 4.

DETAILED DESCRIPTION OF THE INVENTION

Figure 1A:
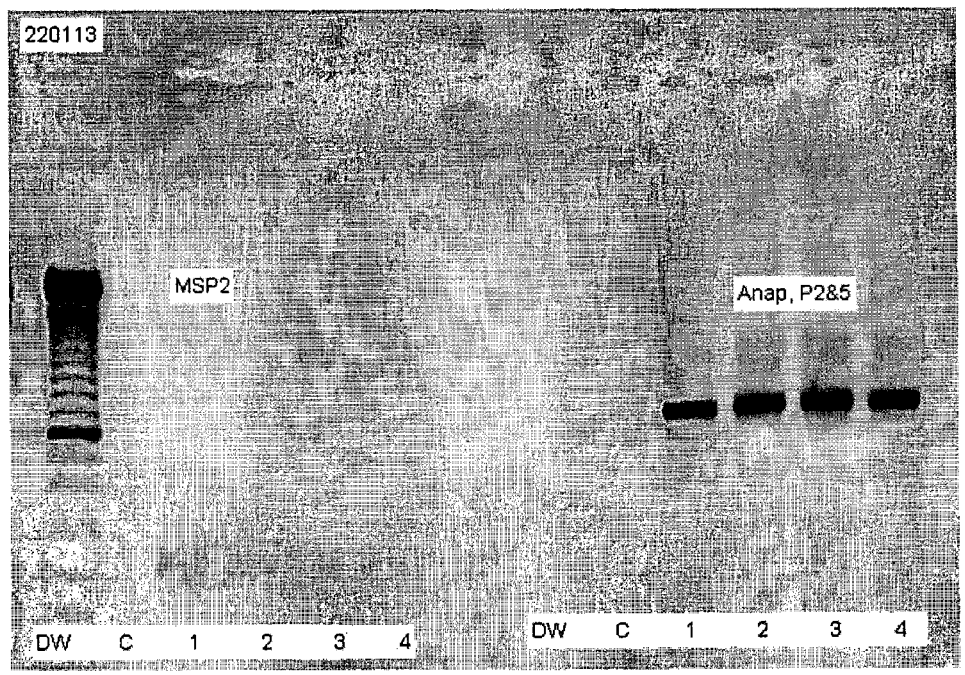
FIGS. 1(A) and 1(B) were produced on different dates. Lane numbers 1 and 2 are duplicates (from HIV-negative source) and lanes 3 and 4 are duplicates (from HIV-positive source). All DNA samples were extracted from a third passage HL60 cells exposed to an agent originating from red blood cells of HIV-negative or HIV-positive patients. These panels represent gel electrophoresis pictures of amplicons obtained by 70 cycles of PCR using primers derived from the *Ehrlichia* MSP2 gene (213 bp) and primers derived from the 16s ribosomal gene of *Anaplasma* (690 bp). The bands on the left sides of FIGS. 1(A) and 1(B) show the 213 bp fragment mapped to human chromosome 7 amplified by the *Ehrlichia* MSP2 primers. The bands on the right sides of FIGS. 1(A) and 1(B) show the 690 bp fragment amplified by the *Anaplasma* primers (SEQ ID NOS: 24 and 25).
Figure 1B:
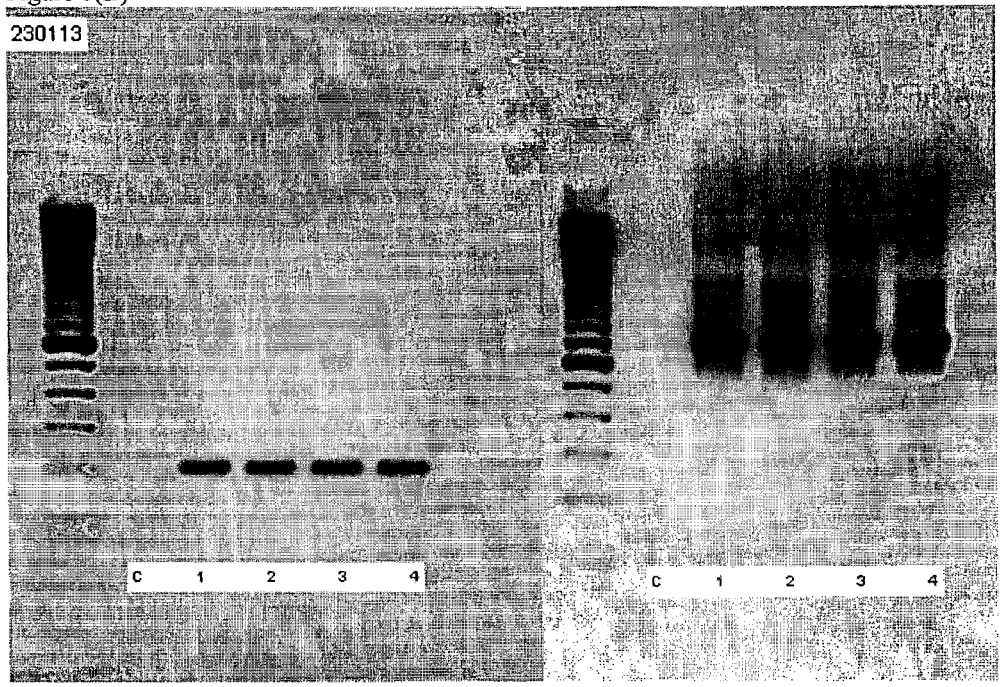

Amplification of DNA from biological samples, including blood, plasma, and serum samples or samples obtained from cell culture can be performed using PCR or other nucleic amplification methods known in the art. These methods can be used to amplify or detect target DNA qualitatively or quantitatively to provide a "yes or no" determination of the presence of the target sequence or to quantitatively detect an amount of DNA amplified under controlled conditions.

The DNA amplified by the first and second kinds of primers is higher frequency in red blood cells obtained from patients infected with human immunodeficiency virus compared to healthy individuals. This is especially the case for patients who have undergone or are undergoing antiretroviral therapy. The quantity of DNA amplified by these primers is reduced after long-term treatment of a patient with antibiotics and the primers were found not to amplify DNA from white blood cells or from other human cell lines. DNA has also been amplified from the red blood cells of healthy African subjects not infected with HIV using these primers. These results suggest the amplified DNA is derived from an antibiotic sensitive microorganism associated with red blood cells.

Despite the apparent human origin of this DNA, the data herein show that the amplified sequences are associated with a transmissible agent and that the transmissible agent is closely associated with human immunodeficiency virus as explained below.

These sequences were easily detected in the DNA of anucleated red blood cells (RBCs) in 100% (35 out of 35 subjects) HIV-infected African and Caucasian patients and they could not be detected in the DNA of nucleated cells including in the white blood cell fraction of the same patients, nor in human DNA from cultured human cells.

These sequences were rarely detected in the red blood cell fraction of healthy African subjects and none were detected in the red blood cells of the healthy Caucasians tested.

Long term antibiotic treatment (e.g., with doxycycline or azithromycin) of HIV-positive patients for more than three months was found to decrease the intensity of the bands amplified using these primers suggesting that these bands are induced, generated or otherwise originate from an antibiotic sensitive microorganism.

Amplification of DNA from a supernatant of a short term culture of human cell line HL60 with an extract of RBC from an HIV-positive patient prepared by freeze-thawing RBC and then by removing heavy components by a low speed (10 mins at 1,500 g) centrifugation produced strong DNA bands. The intensity of these bands suggests growth and multiplication of a microorganism that contains DNA amplified by Primer Pairs 1 and 2.

To further explore this effect, new primers were designed that allow amplification of regions of human genomic DNA adjacent to or including those amplified by Primer Pairs 1 and 2. These new primers include:

primers "hChr1/14179308 S" upstream of, and "hChr1/14179853 AS" encompassing one end of the 237 bp amplicon related to chromosome 1 (546-bp long amplicon);

primers "hChr7/4292976 S" upstream of, and "hChr7/4294619 AS" downstream of the 213 bp amplicon related to chromosome 7 (1,643-bp long amplicon); and the primers described by Appendix 3.

These primers amplify DNA not only from the components of RBCs of HIV infected Caucasian or African patients, but also from the components of RBCs of healthy African subjects. However, these DNAs are lacking in all or most of HIV-negative Caucasian subjects. These sequences are amplified after antibiotic treatment of their carrier subjects indicating that the agent generating them is insensitive to antibiotic treatment. As in the case of the MSP2 primers-amplified sequences, these kinds of primer pairs amplify DNA present in or associated with anucleated RBC and not in white blood cells or human cell lines. It is possible that such a microorganism identified with these primers differs from the carrier of the initial short DNA sequences and will amplify or cause amplification of human genomic DNA sequences in an integrated or unintegrated manner. The primers disclosed herein permit the design of diagnostic tests and treatments aimed at reducing the risk of HIV infection in important segments of the human population in which this agent appears and can be detected by amplification of these DNA sequences.

The third kind of primers that identify a previously unknown bacterial agent that is associated with human red blood cells and related to, but not identical to, known *Rickettsia* species are provided. These primers are derived from the 16S ribosomal DNA sequences of an *Anaplasma* species and amplify a sequence of 700 bp of ribosomal DNA that is about 89% identical to the corresponding regions of the genome of *Rickettsia*. This sequence is about 99% identical to the corresponding regions of *Acinetobacter* genus DNA. Besides the primers exemplified herein, other primers that amplify the same 700 bp of ribosomal DNA or detectable fragments of this sequences may be designed based on this nucleotide sequence. These primers may amplify 20, 30, 50, 100, 200, 300, 400, 500, 600 or 700 nucleotides of this sequence. They may comprise short portions (e.g., 18-30 bp) of the 700 bp sequence and can be designed based on methods well known in the molecular biological arts. The table below depicts the various kinds of primers.

| Appendix 1 | Primers designed based on rickettsiales16S ribosomal DNA gene | SEQ ID NO: | Primers were designed to include a conserved 16S region of DNA which recognizes Rickettsiales and also Propionobacter. |
|---|---|---|---|
| | 5'-GCAAC GCGAA AAACC TTACC | 1 | Rick16S 929S (20 mer) Tm = 45.0° C. |
| | 5'-GACGG GCAGT GTGTA CAA | 2 | Rick16S 1373AS (18 mer) Tm = 45.0° C. |
| Appendix 2 | MSP2 Primers | | |
| MSP2 primer pair 1 | 5' GCCTA CAGAT TAAAG GCT | 3 | 18 mer |
| | 5' ATCAT ARTCA CCATC ACCTA | 4 | 20-mer |
| MSP2 primer pair 2 | 5' CYTAC AGAGT GAAGG CT | 5 | 17-mer |
| | 5' ATCAT ARTCA CCATC ACCTA | 6 | 20-mer |
| Appendix 3 | Human chromosome 1 and 7 primers | | |
| Chromosome 1 primers | | SEQ ID NO: | |
| *primer #1 | 5'-CCT TAC ACT CAG CCA GAC AT | 7 | hChr1/14179308 S |
| *primer #2 | 5'-CCA GGT GTG TGG CTT ATA CA | 8 | hChr1/14179853 AS |
| primer #3 | 5'-CAT AGC TTC CTA GTA AGT AGA CCA G | 9 | hChr1/14180006 S |
| primer #4 | 5'-AGG GGA GTC TGA GAT GGT | 10 | hChr1/14180401 AS |
| primer #5 | 5'-ACT GGA GAG GTG GAG GTT | 11 | hChr1/14181093 AS |
| primer #6 | 5'-GGT AAT TCC TAT GTG CGA GGT | 12 | hChr1/14181390 AS |
| primer #7 | 5'-TCA AAA GAC AGT GGT GAC TCT | 13 | hChr1/14177990 S |
| primer #8 | 5'-ATG TCT GGC TGA GTG TAA GG | 14 | hChr1/14179327 AS |
| Chromosome 7 primers | | SEQ ID NO: | |
| primer #1 | 5'-ATG TAG TTG AGC AGT TTT GAA TGA | 15 | hChr7/4292976 S |

-continued

| | | | |
|---|---|---|---|
| primer #2 | 5'-TCC TGC CTT AGT GAG GAT CT | 16 | hChr7/4293490 S |
| primer #3 | 5'-ATG AAT AGG TGA TGG TGA TGA CT | 17 | hChr7/4293941 AS |
| primer #4 | 5'-CCG TCA TTT AAG CCT TTA ATC TCA | 18 | hChr7/4294102 S |
| primer #5 | 5'-GTA GTC TTT TGG CAT CTC TTT GTA | 19 | hChr7/4294619 AS |
| primer #6 | 5'-CAG CCT GGA GAA CAG AGT G | 20 | hChr7/4294983 AS |
| primer #7 | 5'-GAT CTA GCA GTT CAT AGG AAG GAA | 21 | hChr7/4295251 AS |
| primer #8 | 5'-GGC TGA AAC AAT GGG GTT TT | 22 | hChr7/4291579 S |
| primer #9 | 5'-TTT AGT AGA CCC CTC GAC CA | 23 | hChr7/4293175 AS |

Appendix 4: Anaplasma 16s rDNA based primers

| | | SEQ ID NO: | |
|---|---|---|---|
| Primer | 5'-CTG ACG ACA GCC ATG CA | 24 | sense |
| Primer | 5'-GCA GTG GGG AAT ATT GGA CA | 25 | antisense |

Specific embodiments of the invention include, but are not limited to those described below.

An agent that is associated with red blood cells, especially mature anucleated red blood cells, that passes through a 0.45 micron filter. This agent may be sensitive or insensitive to a particular antibiotic. Agents sensitive to azithromycin or to a cyclin antibiotic have been identified. This agent contains, induces, excises, or otherwise provides DNA that is amplified by (i) primer pairs 1 (SEQ ID NOS: 3 and 4) or 2 (SEQ ID NOS: 5 and 6), (ii) a pair of primers described by Appendix 3 (SEQ ID NOS: 7-14 or SEQ ID NOS: 15-23), (iii), the pair of primers described in Appendix 4 (SEQ ID NOS: 24 and 25); or a pair primers that amplify at least fifteen, twenty, twenty five, thirty, forty, fifty or more consecutive nucleotides of the same DNA as is amplified by the specific primers described herein.

The amplified DNA may be 80%, 85%, 90%, 95%, 99%, up to and including 100% identical or similar to human DNA, wherein sequence identity is determined by BLASTn using the default setting. Preferred parameters for determining the "nucleotide identity" when using the BLASTN program (Altschul, S. et al., Journal of Molecular Biology 215 (1990), pages 403-410) are: Expect Threshold: 10; Word size: 28; Match Score: 1; Mismatch Score: −2; Gap costs: Linear.

An agent that is associated with red blood cells, passes through a 0.45 micron filter, may be sensitive or insensitive to a particular antibiotic, can be detectable in red blood cells of an HIV patient, but not detectable in the white blood cells of said patient. Such an agent may become detectable in the red blood cells of an HIV-infected patient within the first year after HIV infection or after initiation of anti-retroviral treatment. Such an agent may appear or be associated with the red blood cells of an African subject or European subject who is HIV-negative.

The agent may be a microorganism, such as a bacterium, or a specific kind of bacterium such as *Rickettsia* or *Rickettsia*-like bacteria, *Ehrlichia* or *Anaplasma* or a component thereof. Such an agent may contain a plasmid, episome, or extra chromosomal element comprising human chromosomal DNA that is amplified by MPS2 gene primers; or that is contained in or associated with a red blood cell that contains a plasmid or extra chromosomal element comprising human chromosomal DNA that is amplified by MPS2 gene primers.

Isolated red blood cells may contain the agent as described herein as well as disrupted or lysed red blood cells, such as a supernatant produced by freezing and thawing red blood cells after removing white blood cells and then removing material that pellets by a low speed centrifugation, e.g., for 10 mins at 1,500 g. The red blood cells associated with the agent are detected by amplifying DNA from them using (i) primer pairs 1 (SEQ ID NOS: 3 and 4) or 2 (SEQ ID NOS: 5 and 6), (ii) a pair of primers described by Appendix 3 (SEQ ID NOS: 7-14 or SEQ ID NOS: 15-23), (iii), the pair of primers described in Appendix 4 (SEQ ID NOS: 24 and 25); or a pair primers that amplify at least fifteen, twenty, twenty five, thirty, forty, fifty or more consecutive nucleotides of the same DNA as is amplified by the specific primers described herein.

Another aspect of the invention is the DNA amplified from the agent or from red blood cells associated with the agent. This DNA is can be produced using the primer pairs described herein. The DNA that is present in a red blood cell may be from an infectious or replicating agent per se, from a component of an infectious organism present in the anucleated red blood cell, or from DNA that results from exposure of the red blood cell or its precursor cells to an infectious or replicating agent.

The amplified DNA from a red blood cell may comprise portions of human chromosome 1 or 7 including the sequences described in Appendix 5 or Appendix 6 or fragments of these sequences comprising 10, 20, 30, 40, 50, 100, 200 or more consecutive nucleotides of these sequences.

The DNA according to the invention may be contained or inserted into a vector, such as a plasmid or phage vector containing the isolated or purified amplified DNA. A host cell can be transformed with the isolated or purified amplified DNA from the agent or from red blood cells associated with the agent.

The invention is also directed to a method for detecting an agent as described herein comprising contacting material from anucleated red blood cells of a subject with primer Pair 1, primer Pair 2, or a pair of primers selected from the group consisting of those described in Appendix 3 under conditions suitable for amplification of DNA by said primers, and detecting said agent when amplified DNA is detected.

The primers used in this method may be selected from the group consisting of (i) primer pairs 1 (SEQ ID NOS: 3 and 4) or 2 (SEQ ID NOS: 5 and 6), or (ii) a pair of primers described by Appendix 3 (SEQ ID NOS: 7-14 or SEQ ID NOS: 15-23) or a pair primers that amplify at least fifteen, twenty, twenty five, thirty, forty, fifty or more consecutive nucleotides of the same DNA as is amplified by the specific primers described herein. Alternatively, a set of primers that amplify the same DNA fragment amplified by the two primers described above may be employed. These primers may be designed by methods known in the art and each may comprise 18-30 or more base pairs of the sequence amplified by the primers above.

A method for detecting an agent as described herein comprising: contacting under conditions suitable for amplification of target DNA material from red blood cells of a subject with a primer and detecting or recovering the amplified DNA, where the primers are described by Appendix 4:

```
Primer (sense)
                                    (SEQ ID NO: 24)
5'-CTG ACG ACA GCC ATG CA Primer (antisense)
                                    (SEQ ID NO: 25)
5'-GCA GTG GGG AAT ATT GGA CA.
```

Alternatively, a set of primers that amplify the same DNA fragment amplified by the two primers described above may be employed. These primers may be designed by methods known in the art and each may comprise 18-30 or more base pairs of the sequence amplified by the two primers above.

The biological sample used in the method described above or other methods described herein may be whole blood or a cellular component of whole blood, isolated anucleated red blood cells, isolated red blood cell precursors, such as erythroblasts, bone marrow or spleen cells, or subcellular fractions thereof, such as cellular lysates, supernatants or solid materials. Blood plasma or serum or other bodily fluids or tissues may also be used as a biological sample for the methods described herein. Those of skill in the art can select an appropriate biological sample for performance of PCR or select the appropriate conditions for producing an EMS signalized sample based on the disclosures of the patent applications incorporated by reference above. Representative biological samples include whole blood, isolated RBCs, subcellular components, extracts, or lysates of RBCs or their precursor cells, blood plasma or blood serum, spinal fluid, mucosal secretions, urine, saliva, bone marrow, or tissues.

A method for treating or for reducing the severity of a disease, disorder, or condition associated with the agent comprising treating a patient with an agent that reduces the titer of said agent or that reduces the amount of DNA amplified from a cell associated with it. This method may also comprise treating the patient with one or more antibiotics, such as azithromycin or a cyclin antibiotic; with one or more synthetic or natural immunostimulants, active vaccines, passive vaccines, antioxidants or antibiotics. A patient may also undergo treatment sequentially or simultaneously for viruses or other microorganisms or agents capable of causing an immunodeficient disease, disorder or condition. Treatment may be therapeutic or prophylactic and can include the administration of one or more anti-retroviral drugs or other antiretroviral treatments. The patient may be currently undergoing antiretroviral therapy or therapy to eradicate human immunodeficiency virus infection and treatment for the coinfecting bacterium initiated. Other modes of or supplemental treatments include treating the patient with one or more natural immunostimulants, antioxidants or antibiotics.

The methods described herein may employ samples from subjects or patients of different geographic origins or racial or genetic backgrounds. A subject or patient may be HIV-negative, recently (e.g., less than one year) HIV-positive, a patient who has been HIV-position for more than one or two years, an HIV-positive patient who has undergone or is undergoing anti-retroviral treatments or other kinds of patients who are HIV-positive such as those with AIDS or subjects at risk of becoming HIV-positive, developing AIDS or opportunistic infections. Patients may be of African origin or may have lived in Africa and exposed to biological and environmental agents there. Similarly, a patient may be of European or Caucasian origin or may have lived in Europe or America and exposed to biological and environmental agents there.

The invention is also directed to a method for treating a disease, disorder or condition associated with an agent described herein comprising contacting red blood cells with a substance that reduces the amount of DNA amplified from a red blood cell using (i) Primer Pairs 1 or 2, (ii) primers described by Appendix 3, (iii) or the primers described in Appendix 4 or primer pairs that amplify at least 20 consecutive nucleotides of the amplicons amplified by the primer pairs described above. Such a method for treating a disease, disorder or condition associated with an agent described herein may comprise contacting red blood cells of a subject with a substance that reduces the transmission of said agent to the red blood cell; may comprise replacing the red blood cells in a subject with red blood cells that are not associated with said agent or by stimulating the development of new red blood cells in said subject; or may comprise treating blood or red blood cells with an agent that that degrades, crosslinks or otherwise interferes or inactivates nucleic acids inside of or associated with a red blood cell.

Another aspect of the invention is a method for screening blood for red blood cells from which DNA can be amplified using (i) primer pairs 1 (SEQ ID NOS: 3 and 4) or 2 (SEQ ID NOS: 5 and 6), (ii) a pair of primers described by Appendix 3 (SEQ ID NOS: 7-14 or SEQ ID NOS: 15-23), (iii), the pair of primers described in Appendix 4 (SEQ ID NOS: 24 and 25); or a pair primers that amplify at least fifteen, twenty, twenty five, thirty, forty, fifty or more consecutive nucleotides of the same DNA as is amplified by the specific primers described herein. This method comprises contacting a sample of blood or red blood cells with these pairs of primers and detecting amplified DNA and selecting a blood sample from which DNA was amplified or alternatively selecting a blood sample from which no DNA was amplified. For example, a blood sample from which amplified DNA is detected may be further evaluated or cultured to determine the sensitivity of the red blood cells or the agent associated with them to antibiotic or other therapeutic treatments. Alternatively, a blood sample in from which no DNA is amplified may be assessed as being free of the agent associated with the DNA amplified by these primers.

EXAMPLE 1

Detection of Amplified DNA in Red Blood Cells

Separation of Red Blood Cells

Standard procedures for separating RBCs from buffy coat and other peripheral blood components are known. Peripheral blood was processed on a Ficoll gradient to separate the buffy coat from red blood cells. After such separation it was found that DNA extracted from buffy coat cells was completely negative as determined by PCR using the primers described above while the same primers amplified DNA in the fraction containing the separated red blood cells. While it cannot ruled out that the agent detected is externally associated with the red blood cell membranes, it was found that amplified DNA was only detected in a supernatant prepared by a low speed (1,500 g×10 mins) centrifugation to remove the heavy components of a red blood cell lysate. This lysate was prepared by repeated freeze-thawing of red blood cells isolated from the buffy coat, strong shaking by vortex, and a low speed centrifugation (1,500 g×10 mins). A pellet and supernatant fraction were obtained and tested. The primers described above only amplified DNA in the supernatant fraction, but not in the pellet.

Growth on HL-60 Cells

HL-60 cells are an ATCC cell line of promyelocytic origin. Samples of HL-60 cells at a density of $5 \times 10^5$ cells per ml in RPMI medium supplemented with 10% fetal calf serum were inoculated with the supernatant of the red blood cell lysate described above. This lysate was obtained from the red blood cells of HIV-positive patients after freezing, thawing and vortexing as previously described. After culturing for 3 days at 37° C. the low speed (1,500 g×10 mins) supernatants of the cultures were tested by PCR for DNA amplified using Primer Pairs 1 and 2. DNA was amplified from all of these cultures up to a dilution of $10^4$. The same results were obtained from culture supernatant that was passaged through a 0.45 micron filter.

Effects of Long-Term Antibiotic Treatment

Five HIV-positive patients were maintained on their antiretroviral therapy, but received for at least three months a daily antibiotic treatment (azithromycin 250 mg/day or doxycycline 100 mg/day). Blood samples were fractionated to recover a red blood cell fraction on day 0 and after 3 months of antibiotic. Results indicated that the amount of DNA amplified after 3 months of antibiotic treatment was significantly less than that amplified under the same conditions from the samples obtained on day 0.

Detection of Amplified DNA in Red Blood Cells of African and Caucasian Patients

Blood samples were obtained from African and European Patients who were HIV-negative or HIV-positive. Red blood cells were isolated from buffy coat and other blood components by separation on a Ficoll gradient as described above. Table 1 shows the results of amplification of red blood cell samples from these patients using Primer Pairs 1 and 2. Similar results were obtained using the primers described in Appendix 3. No DNA was amplified using Primer Pairs 3 and 4 for Chromosome 1 and 7 from the red blood cells of one European patient who was HIV-positive for a year or less. This suggests that in some Caucasians that the accumulation of this human DNA in the red blood cell fraction occurs late after infection and possibly under the selective pressure of antiretroviral treatment. However, amplified DNA was detected in this patient using the Primer Pairs 1 and 2 shown in Appendix 2, but the amplified DNA bands were weaker than those for chronically-infected HIV-positive patients.

TABLE 1

| | African | | | | Caucasian | | | | Cultured cells (HL 60) | |
|---|---|---|---|---|---|---|---|---|---|---|
| | RBC: HIV neg | RBC: HIV+ | WBC: HIV+ | RBC from HIV+ treated with antibiotics for 3 mos | RBC: HIV neg | RBC: HIV+ | WBC: HIV+ | RBC from HIV+ treated with antibiotics for 3 mos (0 vs 3 mos) | No extract | HL 60 + RBC extract from HIV+ subject (0 vs 3 days) |
| App. 2 | | | | | | | | | | |
| Pair 1 | rare | 100% | 0% | ↓ | 0% | 100% | 0% | ↓ | – | ↑ |
| Pair 2 Chr 1 | rare | 100% | 0% | ↓ | 0% | 100% | 0% | ↓ | – | ↑ |
| Pair 1 Chr 7 | + | + | – | + | – | + or – * | – | + | – | |
| Pair 1 | + | + | – | + | – | + or – * | – | + | – | |

+ in chronically infected and treated patients
– in recently infected patients

DNA Amplified Using Primer Pairs 1 and 2

MSP2 Primer Pairs 1 and 2 were used to perform PCR on red blood cells of HIV-positive subjects are removal of white blood cells and other blood components by Ficoll gradient separation. Primer Pairs 1 and 2 are shown below.

```
Primer Pair 1
5' GCCTA CAGAT TAAAG GCT        18 mer

5' ATCAT ARTCA CCATC ACCTA      20 mer

Primer Pair 2:
5' CYTAC AGAGT GAAGG CT         17 mer

5' ATCAT ARTCA CCATC ACCTA      20 mer.
```

The DNA bands amplified by PCR using Primer Pairs 1 and 2 were 100% homologous with human sequences (primer sequences excluded) present in data-banks for human genomic sequences, respectively in human chromosome 1 (clone RP11-332J14 GI:22024579, clone RP11-410C4 GI:17985906, and Build GRCh37.p5 Primary Assembly—) and in human chromosome 7 (PAC clone RP4-728H9 GI:3980548; human Build GRCh37.p5, and alternate assembly HuRef SCAF_1103279188381:28934993-35424761).

Human Chromosome 1 and 7 DNA Sequences Described in Appendix 5

Appendix 5 shows the identities of human chromosome 1 and Chromosome 7 sequences that are amplified by primers described in Appendix 3. Primer sequences are underlined.

Primer Pair 3:

Primer "hChr1/14179308 S" upstream of, and "hChr1/14179853 AS" encompassing one end of the 237 bp amplicon related to chromosome 1 (546-bp long amplicon) were used to perform PCR on material from red blood cells isolated from other blood components by Ficoll gradient.

Primer Pair 4:

Primers "hChr7/4292976 S" upstream of, and "hChr7/4294619 AS" downstream of the 213 bp amplicon related to chromosome 7 (1,643-bp long amplicon); and the primers described by Appendix 3.

EXAMPLE 2

Method for Detecting Risk of Acquiring HIV Infection or Opportunistic Infection Associated with HIV Infection or Risk of the Progression of an HIV Infection or Opportunistic Infection Blood is collected from a subject in the presence of EDTA as an anticoagulant. The red blood cells in the sample are separated from buffy coat and plasma components of blood using a Ficoll-Hypaque gradient according to the manufacturer's current protocol. DNA in the red blood cell sample is prepared and amplified using a QIAGEN® Fast Cycling PCR Kit or Taq PCR Core Kit (as described in the current QIAGEN® product catalog) using MSP2 primer pair 1: 5' GCCTA CAGAT TAAAG GCT (SEQ ID NO: 3) and 5' ATCAT ARTCA CCATC ACCTA (SEQ ID NO: 4) or MSP2 primer pair 2: 5' CYTAC AGAGT GAAGG CT (SEQ ID NO: 5)+5' ATCAT ARTCA CCATC ACCTA (SEQ ID NO: 6).

Amplified DNA is resolved by gel electrophoresis and detected by staining with ethidium bromide.

A subject is classified as being at a higher risk for acquiring HIV or HIV-associated opportunistic infection or for when amplified DNA is detected.

EXAMPLE 3

Method for Detecting Microorganism Associated with Risk or Progression of HIV Infection or Opportunistic Infection Associated with Infection with HIV Blood is collected from a subject in the presence of EDTA as an anticoagulant. The red blood cells in the sample are separated from buffy coat and plasma components of blood using a Ficoll-Hypaque gradient according to the manufacturer's current protocol. DNA in the red blood cell sample is prepared and amplified using a QIAGEN® Fast Cycling PCR Kit or Taq PCR Core Kit (as described in the current QIAGEN® product catalog) using the primer pair 5'-CTG ACG ACA GCC ATG CA (SEQ ID NO: 24)+5'-GCA GTG GGG AAT ATT GGA CA (SEQ ID NO: 25).

Amplified DNA is resolved by gel electrophoresis and detected by staining with ethidium bromide.

A subject is identified as being infected with a microorganism when amplified DNA is detected.

APPENDIX 5

The human chromosome 1 sequence amplified by the MSP2 primers shown below:

| primer identifiers | sequences | | |
|---|---|---|---|
| MSP2 primer #3)Ac/mMSP2-1019S | 5'-CYTACAGAGTGAAGGCT | where Y = T or C | (SEQ ID NO: 5) |
| MSP2 primer #5)Ac/mKSP2-1128AS | 5'-ATCATARTCACCATCACCTA | where R = G or A | (SEQ ID NO: 6) |

Sequence of the 237 bp amplicon (SEQ ID NO: 26) generated with these two primers by PCR:

5'-<u>ATCATAGTCACCATCACCTA</u>CCAGCTGTATAAGCCACACACCTGGGAGTCCTCCTAGCCTTTTTCCTCCTCCTCTCATC
CTCCATATCCCATTGACCGTCAGGGCCTACTGAGTCTACACTCCAATTTTCTTTTAAATCTATCCCCACTGCCACTGTCCTA
GTCTAAGGCAATACCATCTGGTCACCCAGATCATTCCATAGCTTCCTAGTAAGTAGACCAGCCTTCACTCTGTAAG-3' underlined nucleotides: primer sequences bold nuleotides: divergent nuleotides between MSP2 primers and the corresponding homologous human Chr 1 sequence.

The human chromosome 7 sequence amplified by the MSP2 primers shown below:

```
                    primer indentifiers sequences

MSP2 primer #2)AphMSP2-1019S      5'-GCCTACAGATTAAAGGCT    (SEQ ID NO: 3)
MSP2 primer #5)Ac/mMSP2-1128AS    5'-ATCATARTCACCATCACCTA where R = G or A (SEQ ID NO: 6)

Sequence of the 213 by amplinon (SEQ ID NO: 27) generated with these two primers by PCR :
5'-GCCTACAGATTAAAGGCTTAAATGACGGTGAAAACTTAGTATTCTTTGGGTGGACAATAGTGAAATTTGC
ACTTTGGACAGAATGACATGTACAAAAAGAGTCAAGAAACTTTTTAATCTATTTAAAGGACTCAAAGTAATTT
GTGAAGGCCATAGCGTAAAAATAACTTCAGTGGATGGAATGGGATGATGAATAGGTGATGGTGACTATGAT-3'
``` underlined nucleotidese: primer sequences
bold nucleotides : divergent nucleotides between MSP2 primers and the corresponding homologous human Chr 7 sequence.

Identities of the human sequences amplified by the human chromosome 1 primers or human chromosome 7 primers described in sections A) and B) respectively below.

The sequences described below, except for the primers and MSP2-derived amplicons, are corresponding to human genomic sequences available in NCBI genome databanks (www.ncbi.nlm.nih.gov/projects/genome).

A) Genomic human Chromosome 1 primers #1 (hChr1/14179308 S) and #2 (hChr1/14179853 AS) PCR-amplified 546 bp amplicon (SEQ ID NO: 28):
identifier: Amplicon hChr1/14179308-14179853
5'-CCTTACACTCAGCCAGACATATTTGTGTTTGTTATCCATGTCACAGAGACTTTGGCATTTCTGGGTGAGGAGAAGAGAAGAGAATACATGGAAACCCAGGGTAAGAGAAAAGGACAACAGAGAATGT
GGCATGGGGAATGCTCTGCTGGGTCACATTGAATGTTCTGAACCACTGTGAAAAAAGGAGTTAGAAAGAATCAGATGCCGAAGGAGCCAATTTCACAATACTCCGAGACTCCAGGGCAAAGCAGCCTTGTTCTA
GTAGCCTATGGTAAAAGAGAACAGAGACTGAGGGGAGGACTTTTCCCCTGAGTCCACCACACAAACCGCCATGGAGCCTGAAGTCTCAGGGAGCAGCCTGAAGCTCAGGGGACGCATGGGAGGGATTTGCCTTTTGAATTCTCCAATGGG
ATGTCTTACAGGCACTTCATATTTAGCAGATCCAAAACTTAACTCAGATACTCCTTGCCATATCTGTTCCCTGTGTTCCTGACCATGATTATCACCATCACTCACCAGCTGTATAAGCCACACACCTGG-3'
underlined nucleotides: hChr1 genomic primer sequences
bold nucleotides: homologous extremity of the 237 bp amplicon obtained with the primers MSP2#3-5.

B) Genomic human Chromosome 7 primere #1 (hChr7/4292976 S) and #5 (hChr7/4294619 AS) PCR-amplified 1,644 bp amplicon* (SEQ ID NO: 29):
identifier: Amplicon hChr7/4292976-4294619
5'-ATGTAGTTGAGCAGTTTTGAATGAGTTTCTTAATCCTGAGTTCTAGTTTAAGAAAATATTAAGAAAATATTACACCAACTAAAATTTTACTGCAGATAATCATAAGTTGGTTAGATTGGACCTTCATT
GTGAAATGCAGTAACTTTGGTTTAAGCAATATCCAAAACCAGAAATTGGTGCGAGGGGTCTACTAAATTCCGTTTCTTTGTTCTAAACAATTAAACATTCTAAAATTTAGGGAAAAGGACCAATGGTGCAAACATTT
TAGAGCTGACGAGTTGTGTGCCATATGCCATGATTCTGTTTACAAATGAACAGTATTCAGATTCAAAATCAGTGTAAACACTGTGTGTGTGTGTGTGTGTATTTTACACAGCCATTTA
AATATTAACCGCCTTTGAGTATTAGGGGGAAAAAACAGAAATCAAAAAGCGAATATTGTTGTTTCCTGAATCCTCCCACCAAACCACTTTTAAATTAATTATATTCCTGCCTTAGTGAGGATCTTTCCTATTCATCAAA
GATAAAATACCAAAATATAATTTACTCCTCCTTCCTACCTCTCTCTACCTTTATTTTCCTCTATTTATTTGATTTTACTTCTCTCTCAGTGCATCCTTACTTGTCTCTCAGTGTGCTCTAGTTTCTGGCCTCATGTCTCTTT
CCAATAAATACTTCCTCCAGGGCTTCAGCAGTGTATATTGCAATCCATGAGTGTGATGCCCATTGACAGGGCACAAACCAGGCAAACATACACAATACACAGTCATTATCAATCAATCAAATGACCATATAATCATAACAGTCATTACTGTGCCTTTACT
TCATCATCCCATTCCATTCCATCCATCGAGTGTATATTTACGCTATGGCCTTTAACTCTGAGTCCTTTAAATAGATTAAAAAGTTTCCTTATATGTCATGATTAAAATACAATCACTCTTTCTGCTTGCTTGAGCATAATTTTAATGTCTAACTATTCTGTAATTA
TCCACCCAAAGAATACTAAGTTTCACCGTCATTAAGCCTTTAATCTCAGGATCTCACAATAAATCAGGGATATTGTTTATGATGAATTCCCCATCACAATACTTCACATGTAGTTATCTGCTAGTTATCTGTCAAGATTAAGAAAATTTTATTGAA
TATATATATTTGTACATATAATAAAACTTTAATATAATAAAATGTTTCTTTGAGGGGGAGATTTTCTTTGTAAAACTATCCTTCTGCCTATTAAAATCAGAATACACAGATCTGTATCTGTACAAAGAGATGCCAAAAGACTAC-3'
ATTAATTGTACATATAATAATAATAATAAAACTTTAATAATAAAAATGTTTCTTTGAGGGGAGATTTTCTTTGTAAAACTATCCTTCTGCCTATTAAAATCAGAATACACAGATCTGTATCTGTACAAAGAGATGCCAAAAGACTAC-3'
underlined nucleotides: hChr7 genomic primer sequences
bold nucleotides: homologous sequence of the 213 bp amplicon obtained with the primers MS2P2#2-5.
The internal underlined nucleotides correspond to the sequence of primer hChr7/4293490 S (hChr7#2).
*please note that this amplime lenght has been reported as 1,643 bp long in previous documents. The correct lenght is 1,644 bp.

Other amplicons obtained from HIV positive or HIV-negative patients or from both using the human chromosome 1 or human chromosome 7 primers described in sections C) and D) below.

C) Genomic human Chromosome 1 primers #3 (hChr1/14180006-14180401 AS) and #4 (hChr1/14180401 AS) PCR-amplified 396 bp amplicon (SEQ ID NO: 30):
Identifier: Amplicon hChr1/14180006-14180401
5'-<u>CATAGCTTCCTAGTAAGTAGACCAGCCTTCAGT</u>CTGAGCCCTTCAGTCGAGTGCTGCTGGAGTAATCCTTCCTCCCCAGTCAGGTCACTGCGCTCAAATGATGTCAGCGGCTTT ATCATCCATGTTGCCTGGCTTTTCCTCCTCCCCCTCTCATTTGAGCCATGTCTGCAGCTCCCATACTTATCTTCTCAACACAACTCTCTTCATTCTTGTATCCTCCTCAATTCTCTCAACACAATGAAAAGCAGGTCACTGCGCTCAAATGATGTCAGCGGCTTT TTTCTCTTTTTCCTCCCTCTCATTTGAGCCATGTCTGCAGCTCCCATACTTATCTTCTCAACACAACTACTCTTTGAAATGTTTATTTCAAGGGTTCTTCTATCTTTTAAACCATTCTCAGATCTCCCT-3'
underlined nucleotides: primer sequences
bold nucleotides: homologous extremity of the 237 bp amplicon obtained with the primers MSP2#3-5.

D) Genomic human Chromosome 1 primers #3(hChr1/14180006 S) and #5 (hChr1/14101093 AS) PCR-amplified 1,088 bp amplicon (SEQ ID NO: 31):
Identifier: Amplicon hChr1/14180006-14181093
5'-<u>CATAGCTTCCTAGTAAGTAGACCAGCCTTCAGT</u>CTGAGCCCTTCAGTCGAGTGCTGCTGGAGTAATCCTTCCTCCCCAGTCAGGTCGCTCAAATGATGTCAGCGGCTTT ATCATCCATGTGCCTGGCTTTTCCACAGGCCATGTCTGCAGCTCTGCAGCTCCCATACTTATCTTCTCCGTCTGAATCCTTCTCTAACACAACACAATGAAAAGCAGGTCACTGCGCTCAAATGATGTCAGCGGCTTT TTTCTCTTTTTCCTCCCTCTCATTTGAGCCTCACAAATTCACTTTAGTTCTGCTTAGACATATGCTCAGTAATATTTGAACTGAATGAATCAATACAGACAGCAAAACTCCAACCCCCAAACCTAAAAAAAATC GTTCCCAATAGTCTAGTATTGTGCTTAGACATATGCTCAGTAATATTTGATGTGTGAACGAATGAATCAATACAGACAGCAAAACTCCAACCCCCAAACCTAAAAAAAATC CAAACTTCCCTTGCCTTGCTCTATTAAGGCAGAATTCTTCCCGTCTCAATAACATAAGACATAAGAACTCACAGAATTAGGAGCACACTGGCTTGTACAACCAACTGCTTATTCATA AGTTAAATCTGGCTTCTGCTATTATTGCCTTCTCCCCCACTTTTTTTTTGGAGACAGAATCTCCTTGCTGGAATTCAGTCGCTGGATCTGCGTGATCTCCGCTCACCAGGCTTCCACCTCTCCAGT-3'
underlined nucleotides: primer sequences
bold nucleotides: homologous extremity of the 237 bp amplicon obtained with the primers MSP2#3-5.
The sequence of the 396 bp amplicon hChr1/14100006-14100401 (C) is included in the larger size amplicon 1,088 bp Amplicon hChr1/14180006-14181093
The internal underlined nucleotides correspond to the reverse-complement sequence of primer hChr1/14180401 AS (hChr1#4).

E) Genomic human Chromosome 7 primers #2 (hChr7/4293490 S) and #6 (hChr7/4294983 AS) PCR-emplified 1,494 bp amplicon (SEQ ID NO: 32):
Identifier: Amplicon hChr7/4293490-4294983
5'-<u>TCCTGCCTTAGTGAGATCTTCCTATTCATCAAAGATAAAATAC</u>CAAATATACTTCCTCCAGGGCTTCAGCAGTGTATATTGCAATCATGAGTGTGATGCCCCTATTATTTATTTATTTGATTTACTTCCTATTGTCTCTCAGT GCATCCTTACTACTGGTTCTGGCCTTCAATGTCTCTTTCTTACTGTCGTTTATCCTCCAGGGCTTCAGCAGTGTATATTGCAATCATGAGTGTGATGCCCAACATGTACAACCAGGCACACCAGGCAAACATACACAA TGACCATAATCATACAGTCATTACTGGTGCCTTTATCCATCCATTCATCATCTCCACTAGAATTCCTTTAAGTGAAAATCTGAGTCCTTTAACATTACCGCTATGGCCTTCAACAAATTAAAAGTTCTTGACTCTTTTG GTGAATTTTTATATGAGATAGTCATCACCATACTAAGTGCAAAGTGCAAATTTCACTATTGTCCACCGTCTCTCCACAGATCTCACAATGAAGATCCACAAGAAGATCCCTATATGCCTAATCTTCTGC TACAGTGTCATTCATTCGTCCAAAGTGCAAATTTCACTATTGTCACCGTCTCTCCACAGATCTCACAATGAAGATCCTTCTAATTCAGGGTTGTTGAAATCAGGGTAAGTAGTTCTCCATCACAATA TTGAGCATAATAATTAATGTCTAACTATCTGTAATTATCCTGTAATTATATATTAATTGAAATTGTACATATATATTAATAATAATAATCTCAGACATCTCTTCAAATCAGCTGAATTCCCCATCACAATA CTTCACACATGTAGTAGTTATCAGTCACCAATTTCACCACCATTGAATGCAAATGAACTTCATACCAAAGTGTAAATCTGTGTATTGCCCTCCTCAATCCAGATCTGTAATCAGAATCACAGATCTG TCTAATGTCTTGCTGCAAGATTAAGGAGAAATGTATTGAATGCAAATGAACTTCATACCAAAGTGTAAATCTGTGTATTGCCCTCCTCAATCCAGATCTGTAATCAGAATCACAGATCTG TATCTGTACAAAGAGATGCCAAAAGACTACTTTCATGCTGCAACATGATTATGTGCCCCAAAACTGGATATTTTAATAATAATAATCTCAGCTACTCTTTAAATAGTATCAGATCGAAGGCTGAAGGCTAAAGAAATTA

```
GTAATACTGATGCTCCCTTTATTTAAACTTTTAAGACTTTTATCATGGCATTAAATTTTGACTTTTAAAAATATTATCATTTTTTTTTTTTTTTTTTTTTTTTTGGACCCCCTTAAATTTTGTTCCCGAGTTGAATGCCTCACTGGGACTTGGGTGA

ATGAATGCTCACCCTAGTCCTAGATTAGTACTCATCTTAAATACTGTTAGTTTGGGGTGGTTTTTTTTTTTTTTTTGACAGAGCCTCACTCTGTTCTCCAGGCTG
``` underlined nucleotides: hChr7 genomic primer sequences
bold nucleotides: homologous sequence of the 213 bp amplicon obtained with the primers MSP2#2-5.
A part of the sequence 1,644 bp Amplicon hChr7/4292976-4294619 (B) is included in the amplicon 1,494 bp Amplicon hChr7/4293490-4294983 (E).
The internal underlined nucleotides correspond to the reverse-complement sequence of primer hChr7/4294619 AS (hChr7#5).

For legibility, enlarged versions spanning two side-by-side pages of the sequences shown in Appendix 5 above are provided below. The human chromosome 1 sequence amplified by the MSP2 primers shown below:

```
                primer identifiers   sequences

MSP2 primer #3)  Ac/mMSP2-1019S       5'-CTTAACAGAGTGAAGGCT   where Y = T or C
MSP1 primer #5)  Ac/mMSP2-1026AS      5'-ATCATARTCCCATCACCTAA where R = G or A Sequence of the 237 bp amplicon generated with these two primers by PCR:
5'-ATCATAGTCACCATCACCTACCAGCTGTATAAGCCACACACCTGGGAGTCCTCCTAGCCTTTTCCTCCT
CCTCTCATCCTCCATTCCCATTGACCGTCAGGGCCTACTGAGTCTACACTCCAATTTTCTTTTAAATCTATC
CCCACTGCCACTGTCCTACTCTAAGGCAATACCATCTGGTCACCCAGATCATTCCATAGCTTCCTAGTAAGT
AGACCAGCCTTCACTCTGTAAG-3'
``` underlined nucleotides: primer sequence
bold nucleotides: divergent nuleotides between MSP2 primers and the corresponding homologous human Chr 1 sequence.

The human chromosome 7 sequence amplified by the MSP2 primers shown below:

```
                primer identifiers   sequences

MSP2 primer #2)  AphMSP2-10196        5'-GCCTACAGATTAAAGGCT
MSP1 primer #5)  Ac/mMSP2-1128AS      5'-ATCATARTCACCATCACCTA where R = G or A (same as above)

Sequence of the 213 bp amplicon generated with these two primers by PCR:
5'-GCCTACAGATTAAAGGCTTAAATGACGGTGAAAACTTAGTATTCTTTGGGTGGACAATAGTGAAATTTGC
ACTTTGGACAGAATTTTTAATCTATTTAAAGGACTCAAAGTAATTTGTGAAGGCCATAGCGTAAAATAACTTC
AGTTGACATGTACAAAAAGAGTCAAGAAACGGATGGAATGGGATGATGAATAGGTGATGGTGACTATAGAT-3'
``` underlined nucleotides: primer sequence
bold nucleotides: divergent nuleotides between MSP2 primers and the corresponding homologous human Chr 7 sequence.

Identities of the human sequences amplified by the human chromosome 1 primers described in section A) below.

A) Genomic human Chromosome 1 primers #1 (hChr1/14179308 S) and #2 (hChr1/14179853 AS) PCR-amplified 546 bp amplicon:
indentifier: Amplicon hChr1/14179308-14179853
5'-CCTTACACTCAGCCAGACATATATTTGTGTTTTGTTATCCATGTGCACAGAGACTTTGGCAT

TCTGGGTGAAGGAAGAAAGAAGAGAATATACATGGAAACCCAGGGGTAAGAGAAAAGGACAACAG

AGAATGTGGCATGGGGAATGCTCTGCTGGGTCACATTGAATGGTTCTGAACCACTGTGGAAAAAA

AGGAGTTAGAAAGAATCAGATGCCGAAGGAGCCAATTTTCACAATACTCCGAGACTCAGGGCAAA

AGCAGCCTTGTTCTAGTAGCCTATGGGTAAAAGAAGACACAGAACTGAGGGGAGGACTTTTCCCC

TGAGTCCACCACAAACCGCCATGGAGCTGAGGCAGCCTGAAGTCTCAGGGGCATGGGAGGGATTT

GCCTTTTGGATTTCTCCAATGGGATGTCTTACAGGCACTTCATATTTAGCAGATCCAAAACTTAA

CTCAGATACTCCTCTTGCCATATCTGTTCCTCTTGCTGTGTTCCTGACCATGATTATCACCATCA

CCTACCAGCTGTATAAGCCACACACCTGG-3'

Identities of DNA sequences amplified by Human chromosome 7 primers described in section B) below:

B) Genomic human Chromosome 7 primers #1 (hChr7/4262976 S) and #5 (hChr5/4294619 AS)
PCR-amplified 1,644 bp amplicon*:
identifier: Amplicon hChr7/4292976-4294619
5'-ATGTAGTTGAGCAGTTTTGAATGAGTTTCTTAATCCTGAGTTCTAGTTTAAGAAAATATTAAAAATAAAAATTAT

GTCACCAACTAAATTTTTACTGCAGATAATCATAAGTTGGTTAGATTGGACCTTCATTGTGAAATGCAGTAACTTTGG

TTTAAGCAATATCCAAAACCAGAAATTGGTCGAGGGGTCTACTAAATTCCGTTTTCTTTTGTTCTAAACAATTAAACA

TTCTAAAATTTAGGGAAAAGGACCAATGGTGCAAACATTTTAGAGCTGACAGTTGTGTGCCATATGCCATGATTCTGT

TACAAATGAACAGTATTCAGATTCAAAATCAGTGTAAACACTGTGTGTGTGTGTGTGTGTGTGTGTGTGTGT

-continued

```
GTGTATTTTACACAGCCATTTAAATATTAACCGCCTTTGAGTATTAGGGGAAAAACAGAAACTAAAAGCGAATATATT

TGTTTCCTGAATCCTCCCCACCAAACCACTTTTTAAATTAATTATATTTCCTGCCTTAGTGAGGATCTTCCTATTCAT

CAAAGATAAAATACCAAATATAATTTACTCTCCTTCTCTACCTCACCCCCAATATTCAACAATTCCCTATTTTATTTT

GATTTTACTTCCTATTGTCTCTCAGTGCATCCTTACTACTGGTTTCTGGCCTCAATGTCTCTTTCCATAAATACTTCC

TCCAGGGCTTCAGCAGTGTATATTGCAATCCATGAGTGTGATGCCCTTATAAGCTGTACAGGCACAACCCAGGCAAAC

ATACACAATGACCATAATCATAACAGTCATTACTGGTGCCTTTACTCTGGTTTTATCCATCCCCCAACAATCCTTTAA

TCCTCCACTAGAGTTTATTCTTTTAAGTGAAAATCTGGATTCTTATCTCCCCTAGTATGTATCTCTTAGTGAATTTTT

ATATGAGATAGTCATCACCATCACCTATTCATCATCCCATTCCATCCACTGAAGTTATTTTACGCTATGGCCTTCACA

AATTACTTTGAGTCCTTTAAATAGATTAAAAAGTTTCTTGACTCTTTTTGTACATGTCATTCTGTCCAAAGTGCAAAT

TTCACTATTGTCCACCCAAAGAATACTAAGTTTTCACCGTCATTTAAGCCTTTAATCTCAGGATCTCACAATAAATAC

AATCACTCTTTCCTATATGCCTAATCTTCTGCTTGAGCATAATTTTAATGTGCTAACTATTCTGTAATTATATATATA

TTTTTAATTCAGCCACTTCTCTCACTAGAAAGTGAGTTTGTTGAAATCAGGGTAAGTATATTTTATGTTTGGATGAAT

TCCCCATCACAATACTTCACATGTAGTTATCTAGTCACCAATTTTTATTGAAATTAATTGTACATATAATAAAACTTT

AATATAAAATGTTTCTCTTGAGGGGAGATTTTCTTTGTAAAACTATCCTTCTGAGCTTTGTGATGTGATGATTGTCTA

ATGTCTGTTGCAAGATTAAGGAAAATGTATTTGAATGCAAATGAACTTACACTGTCATACCAAAAGTGTGATAATTTC

TTGCTCCTGAACTCACTCTCCCTACCTGCCTATTAAAATCAGAATACACAGATCTGTATCTGTACAAAGAGATGCCAA

AAGACTAC-3'
underlined nucleotides: hChr7 genomic primer sequences with the primers MSP2#2-5.
bold nucleotides: homologous sequence of the 213 bp amplicon obtained r7/4293490 S (hChr7).
The internal underlined nucleotides corrsepond to the sequence of primer hCh previous
documents. The correct lenght is 1,644 bp.
```

Other amplicons obtained from HIV positive or HIV-negative patients or from both using the human chromosome 1 or human chromosome 7 primers described in sections C) and D) below.

```
C) Genomic human Chromosome 1 primer #3 (hChr1/14180006 S) and #4
(hChr1/14180401 AS) PCR-amplified 396 bp amplicon:
Identifier: Amplicon hChr1/14180006-14180401 AS) PCR-amplified 396 bp amplicon:
5'-CATAGCTTCCTAGTAAGTAGACCAGCCTTCAGTCTGAGCCCTCCTCGGTCCTTCCTCCCCAGTGCT

GCTGGAGTAATCCTTCTAACACAACAATGGAAAGCAGGTCACTGCGGCTCAAATGATGTCAGCGGCTTT

ATCATCCATGTTGCCTGGCTTTTCACAGGCATGTCTTGCAGTGCAGCCTTATAACTCTCTCAACACAAC

TCTGTATCCTCCTCATTCTTCATGCTTTTATAATGTCAAGCCATGTGACACTCCCTAAATATACCATGT

TTCTCTTTTTCCTCCTCCCCCTCTCTCATTTGCAGCTTCCCATACTTATCTTCCTAAACACTACTCTTT

TTGAAATGTTTATTTCAAGGGTTTCTTATCTTTTAAACCATCTCAGACTCCCCT-3'
underlined nucleotides: primer sequence
bold nucleotides: homologous extremity of the 237 bp amplicon obtained with D) Genomic human Chromosome 1 primer #3 (hChr1/14180006 S) and #5
(hChr1/14161093 AS) PCR-amplified 1,088 bp amplicon:
Identifier: Amplicon hChr1/10180006-14181093
5'-CATAGCTTCCTAGTAAGTAGACCAGCCTTCAGTCTGAGCCCTCCTCGGTCCTTCCTCCCCAGTGCT

GCTGGAGTAATCCTTCTAACACAACAATGAAAGCAGGTCACTGCGGCTCAAATGATGTCAGCGGCTTTA

TCATCCATGTTGCCTGGCTTTTCACAGGCATGTCTTGCAGTGCAGCCTTATAACTCTCTCAACACAACT

CTGTATCCTCCTCATTCTTCATGCTTTTATAATGTCAAGCCATGTGACACTCCCTAAATATACCATGTT

TCTCTTTTTCCTCCTCCCCCTCTCATTTGCAGCTTCCCATACTTATCTTCCTAAACACTACTCTTT

TTGAAATGTTTATTTCAAGGGTTTCTTATCTTTTAAACCATCTCAGACTCCCCTGGGGATTACCCCTTT

TCCTATGTTTTATTGTAGCATCCTCACAAATTCACTTTAGTTCCTTCGCATTCTGGTGTCGCTATATA

TTAGTGGGACTATGTCCCCATTAACCTGTTAGATCTCTTGAGAAAAGGGACATGTCTTTTCATCTTGAG

TTCCCCAATACTTAGTATTGTGCTTAGCATATGCTAGGTGCTCAGTAAATATTTGATATGTGTGTGAAC
```

-continued

GAATGAATCAATCAATCAATAAGAAATGACAGACAAACTCCAACCCCCAAACCTAAAAAAAAAAATCC

AAACTTTCCCCTTGCTCTTAGTGTAGATACTGCTCATCAACATAAGGCAAATTCTTCCTGCGCGTCTCA

ATACAGAGGAGGCGAGAACTCACAGAATCACAGAATTAGAGCACTGGCTTTGGCATGAGAACACCCTGA

GTTAAAATCTGGCTTCTGCTATTTATTAGCCACATGACAGTGAATCTCCTTGAGCTTCTGTTTTGTACA

AACTTAAGTTTGGCTTTGTGATCTTATTCCTCTTTGGTGCATCTGTACAACCCAACTGCTTATTCATAT

GACACTGCTAAAACATGCCTTGCCTTCTCCCCCACTTTTTTTTTGGAGACAGAATCTCCCTTTGTCAC

CCAGGCTGGAATTCAGTGGCGTGATCTCGGCTCACTCC<u>AACCTCCACCTCTCCAGT</u>-3'
underlined nuleotides: primer sequences
bold nucleotides: homologous extremity of the 237 bp amplicon obtained
with the primers MSP2#3-5
The sequence of the 396 bp amplicon hChr1/14180005-14180401 (C) is
included in the largers size amplicon 1,088 bp Amplicon hChr1/14280006-1418109
The internal underlines nucleotides correspond to the reverse-complement
sequence of primer hChr1/14180401 AS (hChr1#4).

E) Genomic hmman Chromosome 7 primers #2 (hChr7/4293490 S) and #6
(hChr7/4294983 AS) PCR-amplified 1,494 bp amplicon:
Identifier: Amplicon hChr7/4293490-4294983
5'-<u>TCCTGCCTTAGTGAGGATCTT</u>CCTATTCATCAAATATAAAAATACCAAATATAATTTACTCT

CCTTCTCTACCTCACCCCCAATATTCAACAATTCCCTATTTTATTTTGATTTTACTTCCTATTGT

CTCTCAGTGCATCCTTACTACTGGTTTCTGGCCTCAATGTCTCTTTCCATAAATACTTCCTCCAG

GGCTTCAGCAGTGTATATTGCAATCCATGAGTGTGATGCCCTTATAAGGTGTACAGGCACAACCC

AGGCAAACATACACAATGACCATAATCATAACAGTCATTCTGGCTGCCTTTACTCTGGTTTTATC

CATCCCCCAACAATCCTTTAATCCTCCACTAGAGTTTATTCTTTTAAGTGAAAATCTGGATTCTT

ATCTCCCCTAGTATGTATCTCTTAGTGAATTTTTATATGAGATAGTCATCACCATCACCTATTCA

TCATCCCATTCCATCCACTGAAGTTATTTTACGCTATGGCCTTCACAAATTACTTTGAGTCCTTT

AAATAGATTAAAAAGTTTCTTGACTCTTTTTGTACATGTCATTCTGTCCAAATGTGCAAATTTCA

CTATTGCCACCCAAAGAATACTAAGTTTTCAGCGTCATTTAAGCCTTTAATCTCAGGATCTCACA

ATAAATACAATCACTCTTTCCTATATGCCTAATCTTCTGCTTGAGCATAATTTTAATGTGCTAAC

TATTCTGTAATTATATATATATTTTTAATTCAGCCACTTCTCTCACTAGAAAGTGAGTTTGTTGA

AATCAGGGTAAGTATATTTTATGTTTGGATGAATTCCCCATCACAATACTTCACATGTAGTTATC

TAGTCACCAATTTTTATTCAAATTAATTGTACATATAATAAAACTTTAATATAAAATGTTTCTCT

TGAGGGGAGATTTTCTTTGTAAAACTATCCTTCTGAGCTTTGTGATGTGATGATTGTCTAATGTC

TGTTGCAAGATTAAGGAAAATGTATTTGAATGCAAATGAACTTACACTGTCATACCAAAAGTGTG

ATAATTTCTTGCTCCTGAACTCACTCTCCCTACCTGCCTATTAAAATCAGAATACACAGATCTGT

ATCTG<u>TACAAAGAGATGCCAAAAGACTAC</u>TTTCATGCTGCAACATGATTATGTGCCCCCAAAACC

TGGATATTTATAGTATAGTATCCAGTATTTTCAATCTAAGCTGTACTGGAGCCCGAAGCTAAAGG

AAAATTAGTAATACTGATGCTCCCTTTATTTAAACTTTTAAGACTTTATCATGGCATTAATTTTG

ACPTTTAAAAATATTATCATTTTTTTTGGACCCCCTTAAATTTTGTTCCCGAGTTGAATGCCTCA

CTGGGACTTGGGTGAATGAATGCTCACCCTAGTCCTAGATTAGGTACTCATCTTAAATACTGTTA

GTTTGGGGTGGTTTTTTTTTTTTTTTTTTTTTTTGACAGAGCCT<u>CACTCTGTTCTCCAGG</u>

<u>CTG</u>
underlined nuclectides: hChr7 conomic primer sequences
bold nucleotides: homologous sequence of the 213 bp amplicon obtained
with the primers MSP2#2-5.
A part of the sequence 1,644 bp Amplicon hChr7/4292976-4294619 (B)
is included in the amplicon 1,494 bp Amplicon hChr7/4293490-4294983 (E).
The internal underlines nucleotides correspond to the revierse-complement
sequence of primer hChr7/4294619 AS (hChr7#5).

APPENDIX 6

An amplicon of the 16s rDNA primers (SEQ ID NOS: 24 and 25) is shown below. The amplified DNA originated from the red blood cells of an HIV-negative subject passaged in HL60 cells. Similar DNA is amplified from samples originating from red blood cells of HIV-positive subjects.

```
Amplicon (SEQ ID NO: 33) from HIV-negative subject obtained using primers.
>T56-EMK-4-HIV-_Anae#2-5 wo/ primers seq. = 681 bp
                                                       (SEQ ID NOS: 24 and 25)
GCACCTGTATGTGAATTCCCGAAGGCACTCCCGCATCTCTGCAGGATTCTCACTATGTCAAGACCAGGTAAGGTTCTTCGCGT TGCATCGAATTAAACCACATGCTCCACCGCTTGTGCGGGCCCCCGTCAATTCATTTGAGTTTTAACCTTGCGGCCGTACTCCC CAGGCGGTCTACTTATCGCGTTAACTGCGCCACTAAAGTCTCAAGGACCCCAACGGCTAGTAGACATCGTTTACGGCGTGGAC TACCAGGGTATCTAATCCTGTTTGCTACCCACGCTTTCGAATCTCAGTGTCAATATTATGCCAGGAAGCTGCCTTCGCCATCG GCATTCCTCCAGATCTCTACGCATTTCACCGCTACACCTGGAATTCTACTTCCCTCTCACATATTCTAGCACCACCAGTATCA CATGCAGTTCCCAGGTTAAGCCCGGGGATTTCACATGTGACTTAATGAGCCACCTACACTCGCTTTACGCCCAGTAATTCCGA TTAACGCTCGCACCCTCTGTATTACCGCGGCTGCTGGCACAGAGTTAGCCGGTGCTTATTCTGCAGGTAACGTCTAATCTAAT GGGTATTAACCATTAGCCTCTCCTCCCTGCTTAAAGTGCTTTACAACCAAAAGGCCTTCTTCACACACGCGGCATGGCTGGAT

CAGGGTTGCCCCCCATT
```

---

The invention claimed is:

1. A method for detecting an intracellular microbiological organism having a 16s rRNA gene and capable of passing through a 0.45 micron filter, selectively associated with red blood cells, comprising:
amplifying genetic material consisting essentially of material extracted from the intracellular space of red blood cells of a subject with at least one pair of primers selected from the group consisting of at least one of:
primer pair 1 (SEQ ID NOS: 3 and 4),
primer pair 2 (SEQ ID NOS: 5 and 6),
a primer pair including at least one sense and at least one antisense primer selected from the group consisting of (SEQ ID NOS: 7-14),
a primer pair including at least one sense and at least one antisense primer selected from the group consisting of (SEQ ID NOS: 15-23),
primer pair (SEQ ID NOS: 24 and 25), and
a primer pair that amplifies at least twenty consecutive nucleotides of a DNA molecule amplified by (SEQ ID NOS: 3-25),
under conditions suitable for amplification of nucleic acids of the intracellular microbiological organism by said at least one pair of primers;
quantitatively determining an amplification of genetic material from said amplifying; and
producing at least one signal indicating a detecting of said intracellular microbiological organism when said genetic material is determined to be amplified.

2. The method of claim 1, wherein said at least one pair of primers is selected from the group consisting of
primer pair 1:
5' GCCTA CAGAT TAAAG GCT (SEQ ID NO: 3) and
5' ATCAT ARTCA CCATC ACCTA (SEQ ID NO: 4);
primer pair 2:
5' CYTAC AGAGT GAAGG CT (SEQ ID NO: 5) and
5' ATCAT ARTCA CCATC ACCT A (SEQ ID NO: 6); and
a pair of primers that amplify at least twenty consecutive nucleotides of a DNA molecule amplified by primer pair 1 or primer pair 2.

3. The method of claim 1, wherein said at least one pair of primers is selected from the group consisting of a primer pair including at least one sense and at least one antisense primer selected from the group consisting of primers 1-8 for human chromosome 1 (SEQ ID NOS: 7-14), respectively and a pair of primers that amplify at least twenty consecutive nucleotides of a DNA molecule amplified by said primers 1-8.

4. The method of claim 1, wherein said at least one pair of primers is selected from the group consisting of a primer pair including at least one sense and at least one antisense primer selected from the group consisting of primers 1-9 for human chromosome 7 (SEQ ID NOS: 15-23), respectively and a pair of primers that amplify at least twenty consecutive nucleotides of a DNA molecule amplified by said primers 1-9.

5. The method of claim 1, wherein said at least one pair of primers is selected from the group consisting of the primers (SEQ ID NOS: 24 and 25) and a pair of primers that amplify at least twenty consecutive nucleotides of a DNA molecule amplified by said primers (SEQ ID NOS: 24 and 25).

6. A method for treating or for reducing the severity of a disease, disorder, or condition associated with an microbial endosymbiont capable of passing through a 0.45 micron filter, associated with enucleated red blood cells having a 16s rRNA gene and having DNA sequences amplifiable using polymerase chain reaction using at least one primer selected from the group consisting of (SEQ ID NOS: 1-6 and 24-25), comprising:
treating a patient with an effective amount of a pharmaceutically acceptable formulation of a composition that reduces at least one of:
a titer of said microbial organism, and
an amount of nucleic acids associated with said microbial organism;
performing polymerase chain reaction on nucleic acid consisting essentially of intracellular contents of red blood cells, by using at least one pair of primers consisting of at least one sense primer and at least one antisense primer which amplify a corresponding genetic sequence of the microbial endosymbiont, selected from the group consisting of primers (SEQ ID NOS: 3-25) and a primer pair that amplifies at least twenty consecutive nucleotides of a DNA molecule amplified by (SEQ ID NOS: 3-25); and
determining the reduction in the at least one of the titer of the microbial organism and the amount of DNA associated with said microbial organism by detecting an amplicon from the polymerase chain reaction using said primers.

7. The method of claim 6, wherein said treating comprises comprising treating the patient with one or more antibiotics.

8. The method of claim 7, wherein said one or more antibiotics comprises at least one of an azithromycin and a cyclin antibiotic.

9. The method of claim 6, wherein the amplified genetic sequence comprises human DNA, and said patient is HIV-positive and has or is undergoing antiretroviral therapy or therapy to eradicate human immunodeficiency virus infection.

10. A method for screening blood for red blood cells for a presence of a living microbial organism having a 16s rRNA gene and capable of passing through a 0.45 micron filter, comprising:
contacting a sample derived from an intracellular space of red blood cells from a blood sample of a patient separated from other types of cells, with at least one pair of polymerase chain reaction primers comprising a sense primer and an antisense primer which selectively amplify respective corresponding strands of a nucleic acid of the microbial organism, each selected from the group consisting of (SEQ ID NOS: 3-25) and a primer that amplifies at least twenty consecutive nucleotides of a DNA molecule amplified by (SEQ ID NOS: 3-25)

conducting cycles of polymerase chain reaction to selectively amplify nucleic acid sequences corresponding sequences of said at least one pair of polymerase chain reaction primers; and detecting DNA amplified in the cycles of polymerase chain reaction; and selectively producing an output associated with the detected DNA amplified from a respective blood sample.

11. The method of claim 1, wherein said at least one pair of polymerase chain reaction primers comprises primer pair 1 (SEQ ID NOS: 3 and 4).

12. The method of claim 1, wherein said at least one pair of polymerase chain reaction primers comprises primer pair 2 (SEQ ID NOS: 5 and 6).

13. The method of claim 1, wherein said at least one pair of polymerase chain reaction primers comprises a primer pair consisting of at least one sense primer and at least one corresponding antisense primer selected from the group consisting of (SEQ ID NOS: 7-14).

14. The method of claim 1, wherein said at least one pair of polymerase chain reaction primers comprises a primer pair consisting of at least one sense primer and at least one corresponding antisense primer selected from the group consisting of (SEQ ID NOS: 15-23).

15. The method of claim 1, wherein said at least one primer pair comprises (SEQ ID NOS: 24 and 25).

16. The method of claim 1, wherein the amplified genetic material comprises human genetic material.

17. The method of claim 1, wherein the amplified genetic material comprises a DNA sequence or fragment thereof described by SEQ ID NOS: 26-33.

18. The method of claim 6, wherein said at least one primer comprises primer pair 1 (SEQ ID NOS: 3 and 4) or primer pair 2 (SEQ ID NOS: 5 and 6).

19. The method of claim 6, wherein said at least one primer comprises a pair of primers (SEQ ID NOS: 7-14) or (SEQ ID NOS: 15-23).

20. The method of claim 6, wherein said at least one primer comprises a pair of primers (SEQ ID NOS: 24 and 25).

* * * * *